United States Patent
Horng et al.

(10) Patent No.: US 9,375,153 B2
(45) Date of Patent: Jun. 28, 2016

(54) MOTION/VIBRATION SENSOR

(71) Applicants: INDUSTRIAL TECHNOLOGY RESEARCH INSTITUTE, Hsinchu (TW); NATIONAL SUN YAT-SEN UNIVERSITY, Kaohsiung (TW)

(72) Inventors: Tzyy-Sheng Horng, Kaohsiung (TW); Fu-Kang Wang, Kaohsiung (TW); Kang-Chun Peng, Kaohsiung (TW)

(73) Assignees: INDUSTRIAL TECHNOLOGY RESEARCH INSTITUTE, Hsinchu (TW); NATIONAL SUN YAT-SEN UNIVERSITY, Kaohsiung (TW)

(*) Notice: Subject to any disclaimer, the term of this patent is extended or adjusted under 35 U.S.C. 154(b) by 0 days.

(21) Appl. No.: 14/151,930

(22) Filed: Jan. 10, 2014

(65) Prior Publication Data

US 2014/0128748 A1    May 8, 2014

Related U.S. Application Data

(63) Continuation-in-part of application No. 13/456,849, filed on Apr. 26, 2012, now Pat. No. 8,754,772, which is a continuation-in-part of application No. 12/886,522, filed on Sep. 20, 2010, now Pat. No. 8,698,636.

(30) Foreign Application Priority Data

| May 17, 2010 | (TW) | 99115691 A |
| Oct. 12, 2011 | (TW) | 100136990 A |
| Mar. 18, 2013 | (TW) | 102109406 A |

(51) Int. Cl.
*G08B 23/00* (2006.01)
*A61B 5/0205* (2006.01)
(Continued)

(52) U.S. Cl.
CPC ............. *A61B 5/0205* (2013.01); *A61B 5/0507* (2013.01); *A61B 5/1135* (2013.01); *G01S 13/583* (2013.01); *G01S 13/88* (2013.01); *G08B 13/2491* (2013.01)

(58) Field of Classification Search
None
See application file for complete search history.

(56) References Cited

U.S. PATENT DOCUMENTS

| 3,221,260 A | 11/1965 | Henrion |
| 3,479,607 A | 11/1969 | Ruthroff |

(Continued)

FOREIGN PATENT DOCUMENTS

| CN | 1800876 | 7/2006 |
| CN | 101006915 | 8/2007 |

(Continued)

OTHER PUBLICATIONS

Injection Locking of Microwave Solid State Oscillators by Kaneyuki Kurokawa, IEEE vol. 6, No. 10, Oct. 1973.*

(Continued)

*Primary Examiner* — Ojiako Nwugo
(74) *Attorney, Agent, or Firm* — McClure, Qualey & Rodack, LLP

(57) ABSTRACT

A motion/vibration sensor includes a transmit/receive antenna unit, an oscillation unit and a frequency-mixing unit. The transmit/receive antenna unit receives an output signal from the oscillation unit and transmits a detection signal toward at least one object. The detection signal is reflected by the object as a reflected detection signal and received by the transmit/receive antenna unit. The oscillation unit receives the reflected detection signal from the transmit/receive antenna unit for self-injection locking; and the frequency-mixing unit receives the reflected detection signal from the transmit/receive antenna unit for frequency demodulation. The frequency-mixing unit mixes and demodulates the reflected detection signal from the transmit/receive antenna unit with the output signal from the oscillation unit into a baseband output signal which represents a motion/vibration information.

19 Claims, 5 Drawing Sheets

(51) Int. Cl.
*A61B 5/113* (2006.01)
*G01S 13/58* (2006.01)
*G01S 13/88* (2006.01)
*G08B 13/24* (2006.01)
*A61B 5/05* (2006.01)

(56) References Cited

U.S. PATENT DOCUMENTS

| | | | |
|---|---|---|---|
| 3,670,327 A | 6/1972 | Marsh | |
| 4,109,247 A | 8/1978 | Kaplan | |
| 4,123,755 A | 10/1978 | Fishbein et al. | |
| 4,176,351 A | 11/1979 | DeVita et al. | |
| 4,427,982 A | 1/1984 | Caprio | |
| 4,517,982 A | 5/1985 | Shiga et al. | |
| 4,600,890 A | 7/1986 | Horvat | |
| 4,646,754 A | 3/1987 | Seale et al. | |
| 4,951,060 A | 8/1990 | Cohn | |
| 4,953,010 A | 8/1990 | Cowley | |
| 4,958,638 A | 9/1990 | Sharpe et al. | |
| 4,991,585 A | 2/1991 | Mawhinney | |
| 5,423,076 A * | 6/1995 | Westergren et al. | 455/86 |
| 5,458,124 A | 10/1995 | Stanko et al. | |
| 5,573,012 A | 11/1996 | McEwan et al. | |
| 5,650,749 A | 7/1997 | Main | |
| 5,975,081 A | 11/1999 | Hood et al. | |
| 6,133,802 A | 10/2000 | Ma et al. | |
| 6,369,647 B1 | 4/2002 | Main et al. | |
| 6,369,659 B1 | 4/2002 | Delzer | |
| 6,650,276 B2 | 11/2003 | Lawless | |
| 6,756,936 B1 * | 6/2004 | Wu | 342/175 |
| 7,103,132 B1 | 9/2006 | Baba | |
| 7,314,451 B2 | 1/2008 | Halperin et al. | |
| 7,538,718 B2 | 5/2009 | Ikeda et al. | |
| 7,616,148 B2 | 11/2009 | Wu et al. | |
| 7,656,208 B2 | 2/2010 | Kimura et al. | |
| 7,740,588 B1 | 6/2010 | Sciarra | |
| 7,753,849 B2 | 7/2010 | Morgan et al. | |
| 7,848,896 B2 | 12/2010 | Li et al. | |
| 8,092,389 B2 | 1/2012 | Keilman et al. | |
| 8,103,228 B2 | 1/2012 | Monat et al. | |
| 8,562,526 B2 | 10/2013 | Heneghan et al. | |
| 2004/0150548 A1 | 8/2004 | Walmsley | |
| 2005/0285790 A1 * | 12/2005 | Gagnon | 342/457 |
| 2006/0040739 A1 | 2/2006 | Wells | |
| 2006/0055585 A1 | 3/2006 | Nagasaku | |
| 2007/0126511 A1 * | 6/2007 | Jacobsson et al. | 331/16 |
| 2007/0241864 A1 | 10/2007 | Nagai | |
| 2008/0077015 A1 | 3/2008 | Boric-Lubecke et al. | |
| 2008/0079636 A1 | 4/2008 | Mohamadi | |
| 2008/0119716 A1 | 5/2008 | Boric-Lubecke et al. | |
| 2008/0146944 A1 | 6/2008 | Tao et al. | |
| 2008/0183053 A1 | 7/2008 | Borgos et al. | |
| 2009/0160697 A1 * | 6/2009 | Wu | 342/28 |
| 2009/0203972 A1 | 8/2009 | Heneghan et al. | |
| 2009/0243850 A1 * | 10/2009 | Nishizato | 340/541 |
| 2009/0264761 A1 | 10/2009 | Keilman et al. | |
| 2009/0278728 A1 | 11/2009 | Morgan et al. | |
| 2010/0151799 A1 * | 6/2010 | Kim et al. | 455/73 |
| 2010/0198083 A1 | 8/2010 | Lin et al. | |
| 2010/0240999 A1 | 9/2010 | Droitcour et al. | |
| 2010/0249630 A1 | 9/2010 | Droitcour et al. | |
| 2010/0259305 A1 | 10/2010 | Lee et al. | |
| 2011/0026443 A1 * | 2/2011 | Okada et al. | 370/280 |
| 2011/0137189 A1 | 6/2011 | Kuo et al. | |
| 2011/0215879 A1 * | 9/2011 | Aratake | 331/158 |
| 2011/0279275 A1 | 11/2011 | Horng et al. | |
| 2012/0021698 A1 * | 1/2012 | Borlez et al. | 455/73 |
| 2012/0022348 A1 | 1/2012 | Droitcour et al. | |
| 2014/0016731 A1 * | 1/2014 | Okada et al. | 375/375 |

FOREIGN PATENT DOCUMENTS

| | | |
|---|---|---|
| CN | 101049239 | 10/2007 |
| CN | 101093995 | 12/2007 |
| CN | 101489478 A | 7/2009 |
| CN | 102247146 A | 11/2011 |
| CN | 102499686 A | 6/2012 |
| TW | 373153 | 11/1999 |
| TW | 200706158 | 2/2007 |
| TW | 200913524 A | 3/2009 |
| TW | 201120790 | 6/2011 |
| TW | I347108 | 8/2011 |
| TW | 201143312 | 12/2011 |

OTHER PUBLICATIONS

Phase Noise Self-Injection Locked Oscillator-Theory and Experiment, IEEE transactions on Microwave Theory and techniques by Heng-Chia Chang, vol. 51, No. 9, Sep. 2003.*
Single Antenna Doppler Radars Using Self and Mutual InjectionLocking for Vital Sign detection with Random Body Movement Cancellation by Fu-Kang Wang et. al, IEEE transactions in Microwave theory and technique vol. 59, No. 12, Dec. 2011.*
A novel Vital sign Sensor Based on a Self-Injection-Locked Oscillator, Fu-Kang Wang et. al., IEEE tarnsactions in Microwave Theory and Technique, vol. 58, No. 12, Dec. 2010.*
TW Office Action dated Jul. 11, 2014.
TW Office Action dated Aug. 8, 2014.
Wang, et al.: "Mutual Injection-Locked SIL Sensor Array for Vital Sign Detection with Random Body Movement Cancellation"; Dept. of EE, National Sun Yat-Sen University, Kaohsiung, 804, TW; copyright 2011; pp. 1-4.
Full English machine translation of CN1800876 (Published Jul. 12, 2006).
Full English machine translation of CN101006915 (Published Aug. 1, 2007).
Full English machine translation of CN101049239 (Published Oct. 10, 2007).
English Abstract translation of TW373153 (Published Nov. 1, 1999).
English Abstract translation of TWI347108 (Published Aug. 11, 2011).
English Abstract translation of TW200706158 (Published Feb. 16, 2007).
Chattopadhyay, et al.: "Short Papers"; IEEE Transactions on Microwave Theory and Techniques, vol. MTT-34, No. 4, Apr. 1986; pp. 442-446.
Chuang, et al.: "60-GHz Millimeter-Wave Life Detection System (MLDS) for Noncontact Human Vital-Signal Monitoring"; IEEE Sensors Journal, vol. 12, No. 3, Mar. 2012; pp. 602-609.
Biswas, et al.: "A Doubly Tracking Discriminator"; 978-1-4244-4819-7/09/$25.00 © 2009 IEEE.
Chin, et al.: "A Fast Clutter Cancellation Method in Quadrature Doppler Radar for N oncontact Vital Signal Detection"; 978-1-4244-7732-6/10l$26.00 © 201 0 IEEE; pp. 764-767.
A. Singh, V. M. Lubecke; "A Heterodyne Receiver for Harmonic Doppler Radar Cardio-pulmonary Monitoring with Body-worn Passive RF Tags"; THPD: Biological Effects and Medical Applications of RF and Microwave; IMS 2010 Abstract Cards.
Chattopadhyay, et al.: "A New Microwave Discriminator"; 0-7803-8114-9/03/$17.00 02003 IEEE; pp. 1078-1081.
Wang, et al.: "A Novel Vital-Sign Sensor Based on a Self-Injection-Locked Oscillator"; IEEE Transactions on Microwave Theory and Techniques, vol. 58, No. 12, Dec. 2010; pp. 4112-4120.
Chen, et al.: "An X-Banc Microwave Life-Detection System"; IEEE Transactions on Biomedical Engineering, vol. BME-33, No. 7, Jul. 1986; pp. 697-701.
Park, et al.: "Arctangent Demodulation With DC Offset Compensation in Quadrature Doppler Radar Receiver Systems"; IEEE Transactions on Microwave Theory and Techniques, vol. 55, No. 5, May 2007; pp. 1073-1079.
Main, et al.: "FM Demodulation Using an Injection-Locked Oscillator"; TU3A-1; 0-7803-5687-X/00/$10.000 2000 IEEE; 2000 IEEE MIT-S Digest; pp. 135-138.
Xiao, et al.: "Frequency-Tuning Technique for Remote Detection of Heartbeat and Respiration Using Low-Power Double-Sideband Transmission in the Ka-Band"; IEEE Transactions on Microwave Theory and Techniques, vol. 54, No. 5, May 2006; pp. 2023-2032.

(56) References Cited

OTHER PUBLICATIONS

Tarar, et al.: "Injection-Locked Phase-Locked Loop for BPSK Coherent Demodulation: Theory and Design"; 1-4244-1449-0/07/ $25.00 © 2007 IEEE; pp. 387-390.

Fletcher, et al.: "Low-Cost Differential Front-End for Doppler Radar Vital Sign Monitoring"; 978-1-4244-2804-5/09/$25.00 © 2009 IEEE; pp. 1325-1328.

Lin JC: "Microwave sensing of physiological movement and volume change: a review."; Department of Electrical Engineering and Computer Science, University of Illinois, Chicago 60680; 1992;13(6):557-65.

Pan, et al.: "Null point elimination using RF phase shifter in continuous-wave Doppler radar system"; Electronics Letters Oct. 13, 2011 vol. 47 No. 21.

Droitcour, et al.: "Range Correlation and I/Q Performance Benefits in Single-Chip Silicon Doppler Radars for Noncontact Cardiopulmonary Monitoring";IEEE Transactions on Microwave Theory and Techniques, vol. 52, No. 3, Mar. 2004; pp. 838-848.

Girbau, et al.: "Remote Sensing of Vital Signs Using a Doppler Radar and Diversity to Overcome Null Detection"; IEEE Sensors Journal, vol. 12, No. 3, Mar. 2012; pp. 512-518.

CN Office Action dated Jul. 28, 2015 in corresponding Chinese application (No. 201310118801.3).

TW Office Action dated Apr. 1, 2015 in corresponding Taiwan application (No. 102109406).

TW Office Action dated Jan. 5, 2015 in corresponding Taiwan application (No. 102109406).

SIPO Office Action dated Feb. 5, 2016 in corresponding Chinese application (No. 201310236231.8).

\* cited by examiner

MOTION/VIBRATION SENSOR

This application is a CIP (continuation-in-part) application of U.S. patent application Ser. No. 13/456,849, filed Apr. 26, 2012, now U.S. Pat. No. 8,754,772, which is a CIP application of U.S. application Ser. No. 12/886,522, filed Sep. 20, 2010, now U.S. Pat. No. 8,698,636, which claims the benefit of Taiwan application Serial No. 100136990, filed Oct. 12, 2011, the disclosure of which are incorporated by reference herein in its entirety. This application also claims the benefit of Taiwan application Serial No. 102109406, filed Mar. 18, 2013, the disclosure of which is incorporated by reference herein in its entirety.

TECHNICAL FIELD

The disclosure relates in general to a motion/vibration sensor.

BACKGROUND

Under the influence of social trend in aging population, medical care service and bio-medical electronic devices attract more attention, Remote homecare combined with wireless communication is capable of sensing and recording bio-physiology signals of patients without staying in hospital to save medical resources.

In bio-physiology signal sensing, breath signals and heartbeat signals are very important because they can be used in long term tracking for OSAS (Obstructive Sleep Apnea Syndrome) and irregular heartbeat symptom. OSAS ranks the top three in causes of sudden infant death for a long time, and cardiovascular diseases even have great influence on people's health in developed countries.

Currently, contact type and non-contact type bio-physiology signal sensing apparatuses are used. The contact bio-physiology signal sensing apparatuses perform measurement by touching people's body.

Besides, a motion/vibration sensor is used in security monitoring or identification of person present. The motion/vibration sensor is usually implemented by infrared (IR) technology. However, the motion/vibration sensor implemented by IR technology tends to be affected by environment temperature and, therefore, it may not function properly and it may not be able to perform sensing at all.

A microwave motion sensor detects a frequency shift between a transmission signal and a receiving signal based on Doppler theory. If there is a frequency shift, it indicates that there is a moving target in the environment.

Therefore, the disclosure provides a motion/vibration sensor which detects vibration of thoracic cavity of a user under measurement to analyze bio-physiology parameters (such as breath and heartbeat frequencies) of the user under measurement or detects mechanical vibration frequency of an object.

SUMMARY

According to one embodiment, a motion/vibration sensor in provided. The motion/vibration sensor includes: a transmit/receive antenna unit, an oscillation unit and a frequency-mixing unit. The transmit/receive antenna unit receives an output signal from the oscillation unit and transmits a detection signal toward at least one object. The detection signal is reflected by the object as a reflected detection signal and received by the transmit/receive antenna unit. The oscillation unit receives the reflected detection signal from the transmit/receive antenna unit for self-injection locking and the frequency-mixing unit receives the reflected detection signal from the transmit/receive antenna unit for frequency demodulation. The frequency-mixing unit mixes and demodulates the reflected detection signal from the transmit/receive antenna unit with the output signal from the oscillation unit into a baseband output signal which represents a motion/vibration information.

Figure 1A:
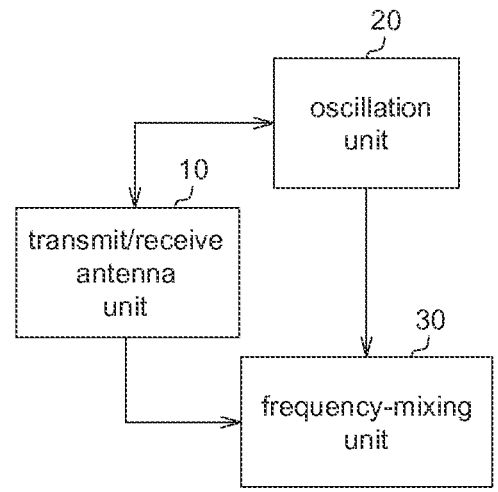
FIG. 1A shows a functional block diagram for a motion/vibration sensor according to one embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Technical terms of the disclosure are based on general definition in the technical field of the disclosure. If the disclosure describes or explains one or some terms, definition of the terms are based on the description or explanation of the disclosure. In possible implementation, in the disclosure, the relationship between objects or events includes a direct relationship or an indirect relationship. The indirect relationship refers to that there are intermediate objects or space between the objects or there are intermediate events or timing period between the events. Further, shapes, sizes and ratios of the objects are exemplary for one skilled person in the art to understand the disclosure, not to limit the disclosure.

Each of the disclosed embodiments has one or more technical features. However, it does not mean that implementation of the disclosure needs every technical feature of any embodiment of the disclosure or combination of the embodiments of the disclosure is prohibited. In other words, in possible implementation, one skilled person in the art would selectively implement part or all technical features of any embodiment of the disclosure or selectively combine part or all technical features of the embodiments of the disclosure based on the disclosure of the disclosure and his/her own need. Implementation of the disclosure is flexible.

The disclosure of the disclosure includes a motion/vibration sensor. The technical features of the embodiments of the disclosure are examples for person skilled in the art to understand the disclosure and not to limit the disclosure. Besides, if the implementations are possible, person skilled in the art may choose equivalent elements or steps to implement the disclosure based on the disclosure of the disclosure. That is, the implementation of the disclosure is not limited by the embodiments disclosed in the disclosure.

If the motion/vibration sensor of this disclosure includes one or more known elements, details of the known elements are omitted in the following description if the full disclosure requirement and the enablement requirement are met.

The motion/vibration sensor disclosed by the embodiments of the disclosure may be used for detecting cardiopulmonary signals of user under measurement in contact or in non-contact. In the following description, a non-contact detection is taken as an example but not to limit the disclosure. The contact detection is also suitable in the embodiments. In the following description, a user is taken as an example of object under measurement, but not to limit the disclosure. Other organisms, machines or any object with motion/vibration feature are also suitable in the embodiments.

The motion/vibration sensor may detect the motion of the user under measurement by transmitting radio frequency waves and/or optical detecting waves. Due to the Doppler effect of the reflection waves reflected from the user under measurement and resulted from the bio-physiology behavior (such as breath and heartbeat) of the user under measurement during a detection period, the radio frequency waves and/or the optical detecting waves from the motion/vibration sensor are modulated and the reflected radio frequency waves and/or the optical detecting waves are injected into an oscillation unit. Therefore, the oscillation unit is in self-injection locking, which performs frequency modulation of the oscillator by the bio-physiology signal of the user under measurement (which is included within the reflected radio frequency waves and/or the optical detecting waves) to make the signal easy to be detected by a frequency-mixing unit. A voltage signal which comes from a down-conversion operation by a frequency-mixing unit is input into a signal processing unit to obtain time domain waveforms and frequency domain signals of the vibration object (for example, the heart and lung of the user under measurement) in the environment for detecting the frequency of the vibration object (for example, the cardiopulmonary signals of the user under measurement).

Now refer to FIG. 1A which shows a functional block diagram for a motion/vibration sensor according to one embodiment of the disclosure. As shown in FIG. 1A, the motion/vibration sensor 100 includes a transmit/receive antenna unit 10, an oscillation unit 20 and a frequency-mixing unit 30.

The transmit/receive antenna unit 10 is electrically connected to or coupled to one of the differential signal output ports of the oscillation unit 20, to receive an output signal from the oscillation unit 20 and to transmit radio frequency transmission signals and/or optical detection waves (which may be referred as detection signals) toward the user under measurement. The radio frequency transmission signals and/or the optical detection waves are reflected by the user under measurement. The reflected radio frequency signals and/or the reflected optical detection waves (which may be referred as reflected detection signal) are received by the transmit/receive antenna unit 10. In one embodiment, the transmit/receive antenna unit 10 is not only electrically connected to or coupled to one of the differential signal output ports of the oscillation unit 20, but also an input port of the frequency-mixing unit 30. In details, the transmit/receive antenna unit 10 sends the reflected detection signals to the oscillation unit 20 so that the oscillation unit 20 is in self-injection locking; and the transmit/receive antenna unit 10 sends the reflected detection signals to the frequency-mixing unit 30 so that the frequency-mixing unit 30 performs frequency demodulation on the reflected detection signals.

The oscillation unit 20 may receive the reflected detection signals from the transmit/receive antenna unit 10 via an independent injection signal port or via either one of the differential signal output port pair of the oscillation unit 20.

An input port of the frequency-mixing unit 30 is electrically connected to or coupled to another differential signal output port of the oscillation unit 20. The frequency-mixing unit 30 mixes the reflected detection signal from the transmit/receive antenna unit 10 and the output signal from the oscillation unit 20. The frequency-mixing unit 30 detects the bio-physiology signals by demodulating the reflected detection signals from the transmit/receive antenna unit 10 for the user under measurement into a baseband output signal (which is a voltage signal). The baseband output signal represents a motion/vibration information.

Figure 1B:
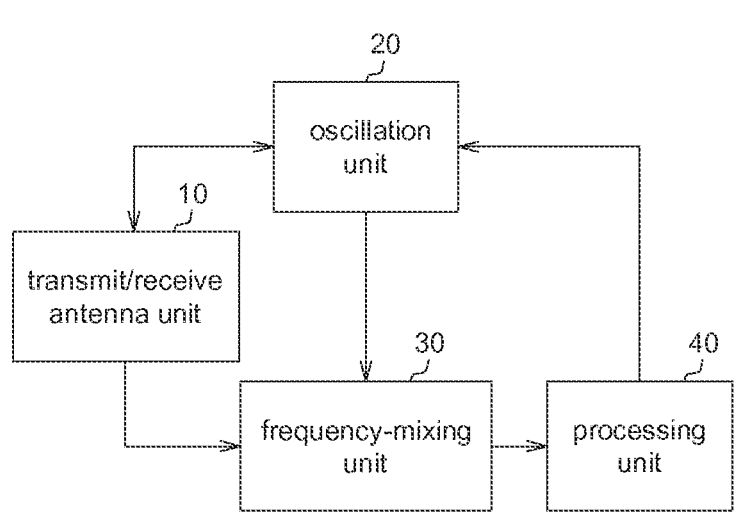
FIG. 1B shows a functional block diagram for a motion/vibration sensor according to another embodiment of the disclosure.

In another embodiment of the disclosure, the motion/vibration sensor may further include a processing unit. FIG. 1B shows a functional block diagram for a motion/vibration sensor 100' according to another embodiment of the disclosure. The motion/vibration sensor 100' further includes a processing unit 40.

That is, the processing unit may be not integrated in the motion/vibration sensor (as shown in FIG. 1A) or may be integrated in the motion/vibration sensor (as shown in FIG. 1B). Further, in other possible embodiment of the disclosure, the processing unit may be at a remote position, and the baseband output signal from the frequency-mixing unit 30 of the motion/vibration sensor may be transmitted to the remote processing unit by wire/wireless transmission, which is still within the scope of the disclosure.

An output port of the processing unit 40 is electrically connected to or coupled to a voltage input port of the oscillation unit 20. The processing unit 40 outputs a control voltage to the oscillation unit 20 to determine an operation frequency of the oscillation unit 20. The processing unit 40 processes the baseband output signal from the frequency-mixing unit 30 (for example but not limited to, digital filtering, amplification, Fourier transformation and so on to obtain the motion/vibration information (for example but not limited to, time domain waveforms and frequency domain signals of the breath and heartbeat of the user under measurement).

Figure 2:
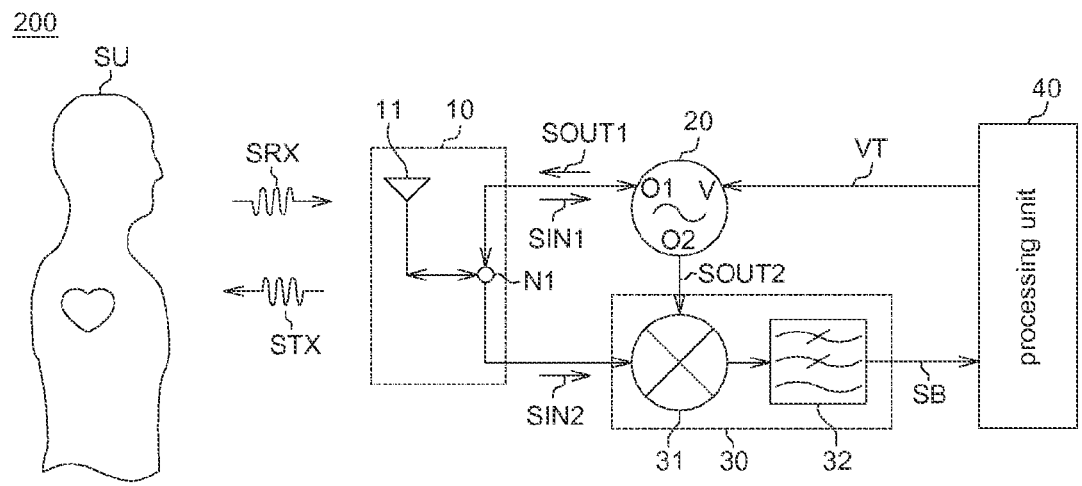
FIG. 2 shows a detailed circuit diagram for a motion/vibration sensor according to one embodiment of the disclosure.

Refer to FIG. 2 which shows a detailed circuit diagram for a motion/vibration sensor 200 according to one embodiment of the disclosure. In this embodiment, the transmit/receive antenna unit 10 includes an antenna 11. The antenna 11 is electrically connected to or coupled to an output port of the oscillation unit 20 and an input port of the frequency-mixing unit 30. In FIG. 2, the antenna 11 is connected to the oscillation unit 20 and the frequency-mixing unit 30 via a node N1. In other possible embodiment, the antenna 11 is coupled to the oscillation unit 20 and the frequency-mixing unit 30 via a circulator or a power divider.

As shown in FIG. 2, the oscillation unit 20 has a voltage input port V, pair of differential signal output ports O1 and O2. The voltage input port V receives an analog control voltage VT from the processing unit 40. In the embodiment, the differential signal output port O1 of the oscillation unit 20 is electrically connected to or coupled to the antenna 11 of the transmit/receive antenna unit 10 so to output an output signal SOUT1 to the antenna 11. The antenna 11 transmits the output signal SOUT1 of the oscillation unit 20 toward the user under measurement SU. In FIG. 2, the signal toward the user under measurement SU is referred as a transmission signal STX. The transmission signal STX is modulated by the motion or vibration of the user under measurement SU based on Doppler effect into a reflected detection signal SRX. The reflected detection signal SRX is received by the antenna 11 as two injection signals SIN1 and SIN2 (basically, the two injection signals SIN1 and SIN2 are the same). The injection signal SIN1 is input into the oscillation unit 20 via the differential signal output port O1 of the oscillation unit 20. The injection signal SIN1 makes the oscillation unit 20 operates in self-injection locking. Another injection signal SIN2 is input into the frequency-mixing unit 30 to be mixed.

In FIG. 2, the frequency-mixing unit 30 has two input ports and one output port. One input port of the frequency-mixing unit 30 is electrically connected to or coupled to the antenna 11. Another input port of the frequency-mixing unit 30 is electrically connected to or coupled to the differential signal output port O2 of the oscillation unit 20, so that the frequency variation of the output signal from the oscillation unit 20 is observed. The output port of the frequency-mixing unit 30 is electrically connected to or coupled to the processing unit 40.

The frequency-mixing unit 30 includes a mixer 31 and a low pass filter 32. The mixer 31 is electrically connected to or coupled to the transmit/receive antenna unit 10 and the oscillation unit 20. The low pass filter 32 is electrically connected to or coupled to the mixer 31 and the processing unit 40. In the embodiment, two input ports of the mixer 31 are electrically connected to or coupled to the transmit/receive antenna unit 10 and the differential signal output port O2 of the oscillation unit 20, respectively. In one embodiment, the low pass filter 32 performs a low-pass filtering on the mixing signal from the mixer 31. In the embodiment, the output port of the frequency-mixing unit 30 is the output port of the low pass filter 32.

In the embodiment, the processing unit 40 is electrically connected to or coupled to the voltage input port V of the oscillation unit 20. The processing unit 40 generates the analog control voltage VT to adjust the output frequency of the oscillation unit 20 for detecting signals in the operation frequency band of the oscillation unit 20. The processing unit 40 is electrically connected to or coupled to the output port of the frequency-mixing unit 30 (i.e. the output port of the low pass filter 32) for performing sampling and signal processing on the baseband output signal SB from the frequency-mixing unit 30, to obtain time domain waveforms and frequency domain signals of the breath and the heartbeat of the user under measurement.

Figure 3:
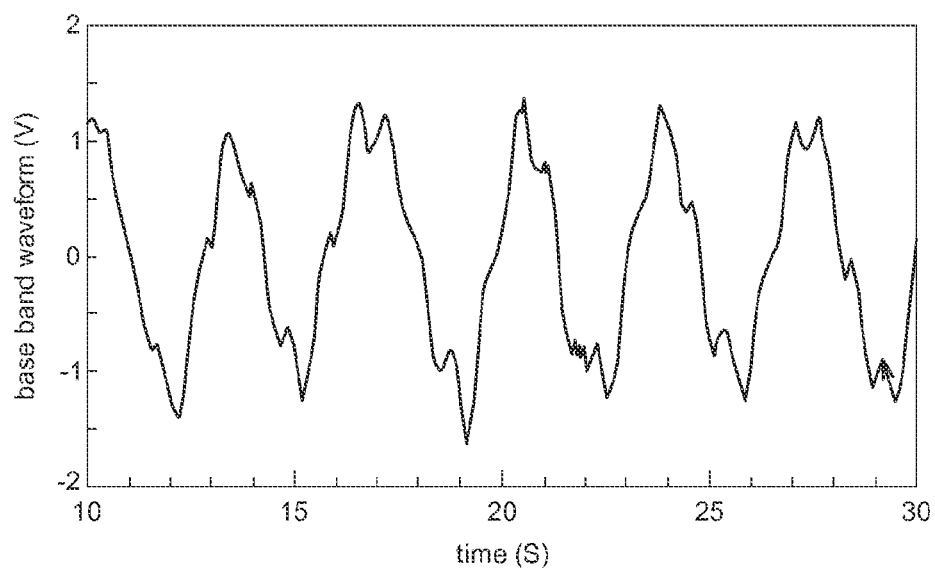
FIGS. 3 and 4 show experimental results according to one embodiment of the disclosure.
Figure 4:
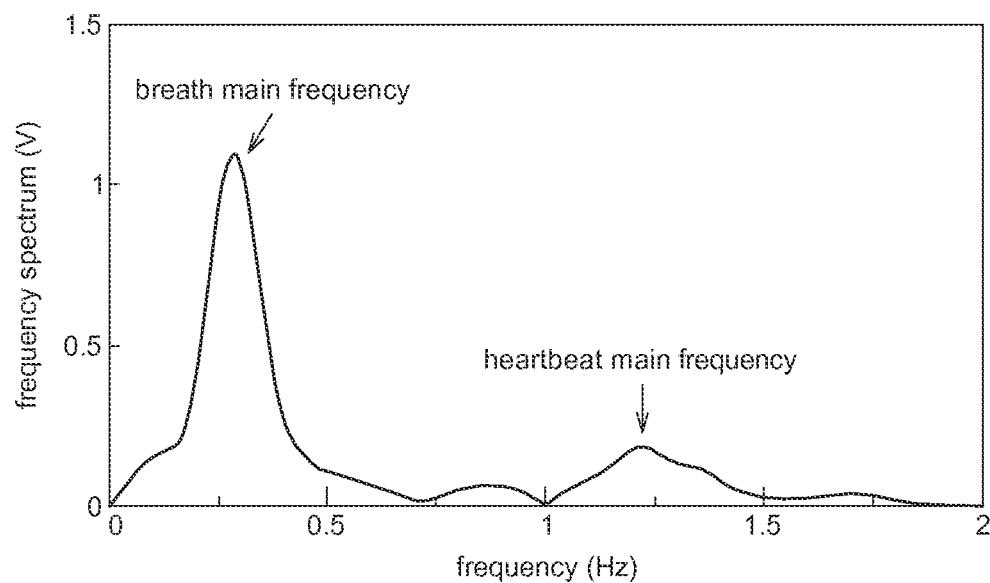

Now refer to FIGS. 3 and 4 which show experimental results according to one embodiment of the disclosure. In the embodiment, the user under measurement, which sits on a chair and breathes uniformly, is away from the sensor/vibration sensor by one meter. The operation frequency of the sensor/vibration sensor is about 2.45 GHz (which is not to limit the disclosure). FIG. 3 shows a time domain waveform which includes bio-physiology information (such as breath and heartbeat). As shown in the frequency spectrum of FIG. 4, after Fourier transformation, the main frequency of the breath and the heartbeat are 0.284 Hz and 1.222 Hz, respectively, i.e. 17 breath/min and 73 heartbeat/min. The detection result of the motion/vibration sensor of the embodiment matches the detection result of other medical instrument.

The disclosure may have other possible embodiments. FIGS. 5A~5D shows possible examples according to other embodiments of the disclosure. Please note that although the motion/vibration sensor FIGS. 5A~5D includes a processing unit, from the above description, the motion/vibration sensor in FIGS. 5A~5D may not include a processing nit, which is still within the scope of the disclosure.

Figure 5A:
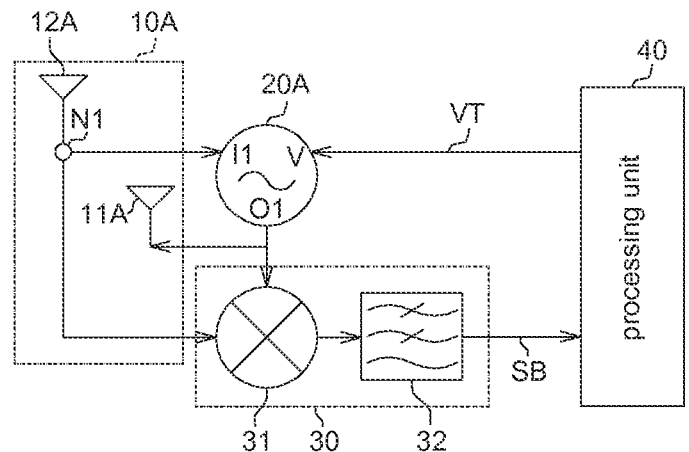
FIGS. 5A~5D shows possible examples according to other embodiments of the disclosure.

In the motion/vibration sensor 100A in FIG. 5A, the transmit/receive antenna unit 10A has two antennas, i.e. a (transmission) antenna 11A and a (receiving) antenna 12A. The single-ended signal output port O1 of the oscillation unit 20A is electrically connected to or coupled to the antenna 11A and the frequency-mixing unit 30. The antenna 11A transmits a radio frequency transmission signal toward the user under measurement. The reflected detection signal (which is reflected from an object) is received by the antenna 12A. The received reflected detection signal is input into the injection signal input port I1 of the oscillation unit 20A and to one input port of the frequency-mixing unit 30 so that the oscillation unit 20A is in self-injection locking and the frequency-mixing unit 30 performs frequency demodulation. The details of the operations of the motion/vibration sensor 100A of FIG. 5A are similarly to that in FIGS. 1A, 1B and 2 and thus are omitted here.

Figure 5B:
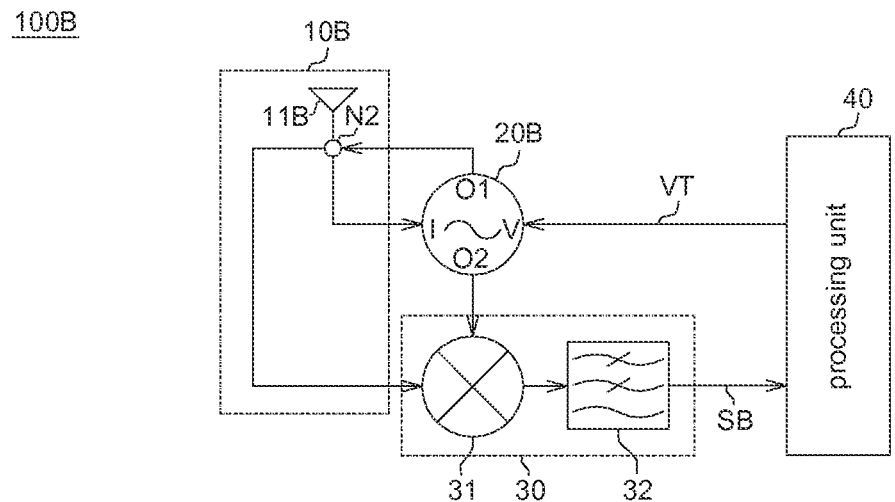

Refer to FIG. 5B. In the motion/vibration sensor 100B of FIG. 5B, the transmit/receive antenna unit 10B has one antenna, i.e. the antenna 11B. The oscillation unit 20B has a voltage input port V, an injection signal input port I and differential signal output ports O1 and O2. The antenna 11B is electrically connected to or coupled to the differential signal output port O1 and the injection signal input port I of the oscillation unit 20B and one input port of the frequency-mixing unit 30. The antenna 11B transmits a radio frequency transmission signal toward the user under measurement (which may be referred as detection signal) and receives the radio frequency transmission signal reflected from the user under measurement (which may be referred as reflected detection signal). After receiving the reflected detection signal, the antenna 11B injects the reflected detection signal to the injection signal input port I of the oscillation unit 20B and the input port of the frequency-mixing unit 30, so that the oscillation unit 20B is in self-injection locking and the frequency-mixing unit 30 performs frequency demodulation. Another input port of the frequency-mixing unit 30 is electrically connected or coupled to the differential signal output port O2 of the oscillation unit 20B. The details of the operations of the motion/vibration sensor 100B of FIG. 5B are similarly to that in FIGS. 1A, 1B and 2 and thus are omitted here. In FIG. 5B, the node N2 is implemented by, for example, a circulator or a power divider.

Figure 5C:
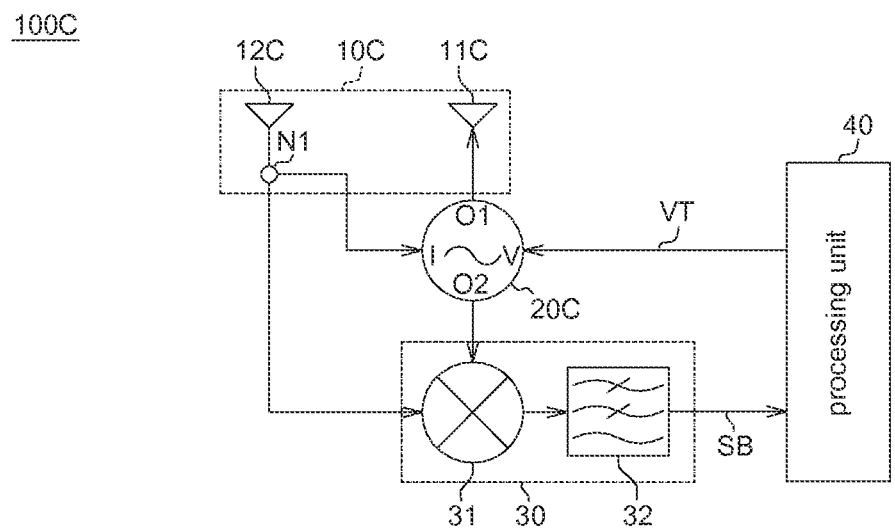

Refer to FIG. 5C. In FIG. 5C, the transmit/receive antenna unit 100 has two antennas, i.e. a (transmission) antenna 11C and a (receiving) antenna 12C. The oscillation unit 20C has a voltage input port V, an injection signal input port I and differential signal output ports O1 and O2. The antenna 11C is electrically connected to or coupled to the differential signal output port O1 of the oscillation unit 20C and transmits a radio frequency transmission signal toward the user under measurement. The radio frequency transmission signal reflected from the user under measurement is received by the antenna 12C. The antenna 12C is electrically connected to or coupled to the injection signal input port I of the oscillation unit 20C and the input port of the frequency-mixing unit 30, so that the oscillation unit 20C is in self-injection locking and the frequency-mixing unit 30 performs frequency demodulation. Another input port of the frequency-mixing unit 30 is electrically connected to or coupled to the differential signal output port O2 of the oscillation unit 20C. The details of the operations of the motion vibration sensor 100C of FIG. 5C are similarly to that in FIGS. 1A, 1B and 2 and thus are omitted here.

Figure 5D:
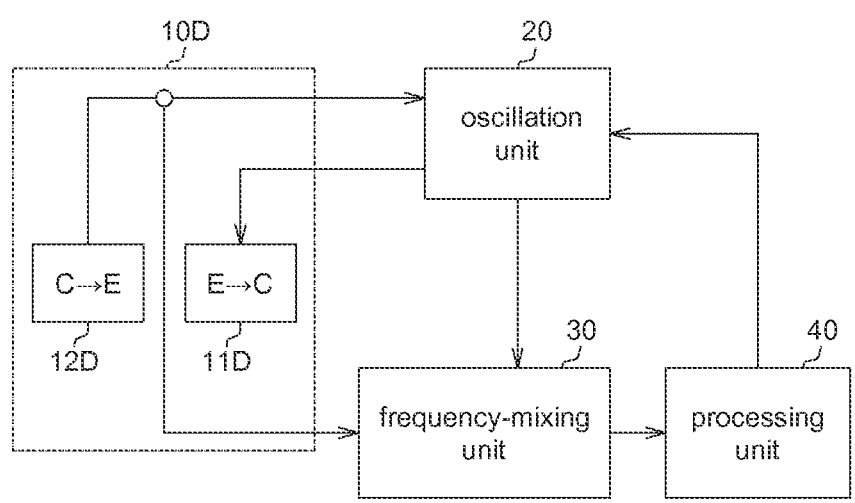

Refer to FIG. 5D, which shows another example of the motion/vibration sensor according to another possible embodiment of the disclosure. As shown in FIG. 5D, what is different from the above-described embodiments relies on that the transmit/receive antenna unit 10D includes an electrical-to-optical converter 11D and an optical-to-electrical converter 12D. The electrical-to-optical converter 11D is electrically connected to or coupled to the oscillation unit 20, for converting the voltage signal from the oscillation unit 20 into an optical wave and for transmitting the optical wave toward the user under measurement. The optical wave is reflected from the user under measurement and received by the optical-to-electrical converter 12D. The optical-to-electrical converter 12D converts the reflected optical wave into a voltage signal and inputs the voltage signal into the oscillation unit 20 and the frequency-mixing unit 30. Details of the oscillation unit 20, the frequency-mixing unit 30 and the processing unit 40 have been described above. Because the electrical-to-optical converter 11D and the optical-to-electrical converter 12D have better SNR (signal-to-noise ratio) in general, the structure in FIG. 5D is more helpful in observing the motion/vibration of the user under measurement.

Still, as discussed above, in the embodiments of the disclosure, the oscillation unit 20 of FIG. 2 has two output terminals but no injection port. The oscillation unit 20A of FIG. 5A has an output terminal but one injection port. Both the oscillation units 20B and 20C of FIG. 5B and FIG. 5C have two output terminals and one injection port. Besides, other possible embodiments of the disclosure could include an oscillation unit which has one output terminal and one injection port.

The conventional continuous-wave radar detects slow motion information (for example, breath and heartbeat) of the object based on a frequency shift between the receiving signal and the transmission signal. Due to phase noise of a signal generator, the conventional continuous-wave radar has a trade-off between the SNR and the system complexity. The conventional continuous-wave radar has acceptable sensitivity at low operation frequency, but at high operation frequency, the increase of sensitivity is limited by the low gain of the receiver components, and the conventional continuous-wave radar is easily affected by noise. Besides, due to reflection waves from other objects in the environment, the baseband signal has a DC (direct current) offset. Therefore, the amplification circuit may be saturated due to the DC offset such that the conventional continuous-wave radar is not capable of effectively detecting the bio-physiology signal.

Another conventional sensor based on a self-injection locked oscillator has high sensitivity at high frequency (when the operation frequency is twice, the sensing distance is quadruple) and is not easily affected by the noise reflected from other objects. However, the conventionally sensor needs a frequency demodulator, and it is difficult to integrate a radio frequency delay unit of the frequency demodulator into a chip at low operation frequency.

On the contrary, in the embodiments of the disclosure, additional transmission delay is provided not only by the transmission of the detection signal in the environment but also by self-injection locking. Thus the radio frequency delay unit of the conventional sensor is not necessary in the embodiments of the disclosure. Further, another feature of the embodiments of the disclosure relies on that inputs of the mixer are coupled to the oscillation unit and the receiving antenna of the transmit/receive antenna unit.

Further, the embodiments of the disclosure utilize the techniques of continuous-wave radar and self-injection locking, and thus could have high sensitivity under different operation frequencies. In high operation frequency, the self-injection locking dominates the motion/vibration detection. In low operation frequency, the motion/vibration detection is performed by continuous-wave radar. The embodiments of the disclosure are basically not affected by environment noise. Besides, the embodiments of the disclosure could not require a radio frequency delay unit, and therefore the integration degree is increased.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A motion/vibration sensor, including:
   a transmit/receive antenna unit;
   an oscillation unit, coupled to the transmit/receive antenna unit; and
   a frequency-mixing unit coupled to the transmit/receive antenna unit and the oscillation unit;
   wherein the transmit/receive antenna unit receives an output signal from the oscillation unit and transmits a detection signal toward at least one object according to the output signal;
   the detection signal is reflected by the object as a reflected detection signal and received by the transmit/receive antenna unit;
   the oscillation unit receives the reflected detection signal from the transmit/receive antenna unit for self-injection locking and the frequency-mixing unit receives the reflected detection signal from the transmit/receive antenna unit for frequency demodulation; and
   the frequency-mixing unit mixes and demodulates the reflected detection signal from the transmit/receive antenna unit with the output signal from the oscillation unit into a baseband output signal which represents a motion/vibration information.

2. The motion/vibration sensor according to claim 1, further including:
   a processing unit, coupled to the oscillation unit and the frequency-mixing unit, for receiving the baseband output signal from the frequency-mixing unit;
   the processing unit controls an operation frequency of the oscillation unit and processes the baseband output signal from the frequency-mixing unit to obtain the motion/vibration information.

3. The motion/vibration sensor according to claim 2, wherein the oscillation unit includes:
   a first one of a pair of differential signal output ports, for outputting the output signal to the transmit/receive antenna unit and receiving the reflected detection signal from the transmit/receive antenna unit;
   a second one of the pair of differential signal output ports, for sending the output signal to the frequency-mixing unit; and
   a voltage input port, coupled to the processing unit, for receiving an analog control voltage from the processing unit.

4. The motion/vibration sensor according to claim 2, wherein the oscillation unit includes:
   a single-ended signal output port, for outputting the output signal to the transmit/receive antenna unit and the frequency-mixing unit;
   an injection signal input port, for receiving the reflected detection signal from the transmit/receive antenna unit; and
   a voltage input port, coupled to the processing unit, for receiving an analog control voltage from the processing unit.

5. The motion/vibration sensor according to claim 2, wherein the oscillation unit includes:
   a first one of a pair of differential signal output ports, for outputting the output signal to the transmit/receive antenna unit;

a second one of the pair of differential signal output ports, for outputting the output signal to the frequency-mixing unit;
an injection signal input port, for receiving the reflected detection signal from the transmit/receive antenna unit; and
a voltage input port, coupled to the processing unit, for receiving an analog control voltage from the processing unit.

6. The motion/vibration sensor according to claim 2, wherein the frequency-mixing unit includes:
a mixer, coupled to the transmit/receive antenna unit and the oscillation unit, for mixing the reflected detection signal from the transmit/receive antenna unit and the output signal from the oscillation unit; and
a low pass filter, coupled to the mixer and the processing unit, for performing a low-pass filtering on a mixing signal from the mixer to generate the baseband output signal and output the baseband output signal to the processing unit.

7. The motion/vibration sensor according to claim 1, wherein the transmit/receive antenna unit includes:
a first antenna, for transmitting the detection signal and receiving the reflected detection signal.

8. The motion/vibration sensor according to claim 1, wherein the transmit/receive antenna unit includes:
a first antenna, for transmitting the detection signal; and
a second antenna, for receiving the reflected detection signal.

9. The motion/vibration sensor according to claim 1, wherein the transmit/receive antenna unit includes:
an electrical-to-optical converter, for converting the output signal from the oscillation unit to an optical detection wave; and
an optical-to-electrical converter, for converting the reflected detection signal into a voltage signal and sending the voltage signal to the oscillation unit and the frequency-mixing unit.

10. A motion/vibration sensor, including:
a transmit/receive antenna unit;
an oscillation unit, coupled to the transmit/receive antenna unit; and
a frequency-mixing unit coupled to the transmit/receive antenna unit and the oscillation unit;
wherein the oscillation unit outputs a first output signal to the transmit/receive antenna unit and outputs a second output signal to the frequency-mixing unit;
the transmit/receive antenna unit receives the first output signal and transmits a detection signal toward at least one object according to the first output signal;
the transmit/receive antenna unit receives a reflected detection signal from the at least one object which reflects the detection signal as the reflected detection signal;
the transmit/receive antenna unit receives the reflected detection signal as a first injection signal and a second injection signal;
the oscillation unit receives the first injection signal from the transmit/receive antenna unit for self-injection locking;
the frequency-mixing unit mixes and demodulates the second injection signal from the transmit/receive antenna unit with the second output signal from the oscillation unit into a baseband output signal which represents a motion/vibration information.

11. The motion/vibration sensor according to claim 10, further including:
a processing unit, coupled to the oscillation unit and the frequency-mixing unit, for receiving the baseband output signal from the frequency-mixing unit;
wherein the processing unit controls an operation frequency of the oscillation unit and processes the baseband output signal from the frequency-mixing unit to obtain the motion/vibration information.

12. The motion/vibration sensor according to claim 11, wherein the oscillation unit includes:
a first one of a pair of differential signal output ports, for outputting the first output signal to the transmit/receive antenna unit and receiving the first injection signal from the transmit/receive antenna unit; and
a second one of the pair of differential signal output ports, for outputting the second output signal to the frequency-mixing unit.

13. The motion/vibration sensor according to claim 11, wherein the oscillation unit includes:
a first one of a pair of differential signal output ports, for outputting the first output signal to the transmit/receive antenna unit;
a second one of the pair of differential signal output ports, for outputting the second output signal to the frequency-mixing unit; and
an injection signal input port, for receiving the first injection signal from the transmit/receive antenna unit.

14. The motion/vibration sensor according to claim 11, wherein the frequency-mixing unit includes:
a mixer, coupled to the transmit/receive antenna unit and the oscillation unit, for mixing the second injection signal from the transmit/receive antenna unit and the second output signal from the oscillation unit; and
a low pass filter, coupled to the mixer and the processing unit, for performing a low-pass filtering on a mixing signal from the mixer to generate the baseband output signal and output the baseband output signal to the processing unit.

15. The motion/vibration sensor according to claim 11, wherein the oscillation unit includes:
a single-ended signal output port, for outputting the first output signal to the transmit/receive antenna unit and the second output signal to the frequency-mixing unit; and
an injection signal input port, for receiving the first injection signal from the transmit/receive antenna unit.

16. The motion/vibration sensor according to claim 11, wherein the oscillation unit includes:
a voltage input port for receiving a control voltage from the processing unit.

17. The motion/vibration sensor according to claim 10, wherein the transmit/receive antenna unit includes:
a first antenna, for transmitting the detection signal and receiving the reflected detection signal.

18. The motion/vibration sensor according to claim 10, wherein the transmit/receive antenna unit includes:
a first antenna, for transmitting the detection signal; and
a second antenna, for receiving the reflected detection signal.

19. The motion/vibration sensor according to claim 10, wherein the transmit/receive antenna unit includes:
an electrical-to-optical converter, for converting the first output signal from the oscillation unit to an optical detection wave; and
an optical-to-electrical converter, for converting the reflected detection signal into a voltage signal and sending the voltage signal as the first injection signal and the second injection signal.

* * * * *